US007819841B2

(12) United States Patent
Horrigan

(10) Patent No.: US 7,819,841 B2
(45) Date of Patent: Oct. 26, 2010

(54) VESSEL ISOLATION DEVICE

(75) Inventor: John B. Horrigan, Beverly, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1834 days.

(21) Appl. No.: 10/920,250

(22) Filed: Aug. 18, 2004

(65) Prior Publication Data

US 2006/0041269 A1 Feb. 23, 2006

(51) Int. Cl.
*A61M 29/00* (2006.01)
(52) U.S. Cl. ...................... 604/104; 623/1.11
(58) Field of Classification Search ............ 604/103.07, 604/104–109, 101.03, 103.01; 623/1.11, 623/1.23, 1.31
See application file for complete search history.

(56) References Cited

U.S. PATENT DOCUMENTS

| 4,423,725 | A |   | 1/1984  | Baran et al. |           |
|-----------|---|---|---------|--------------|-----------|
| 4,636,195 | A |   | 1/1987  | Wolinski     |           |
| 5,090,960 | A |   | 2/1992  | Michael      |           |
| 5,342,306 | A |   | 8/1994  | Michael      |           |
| 5,397,307 | A | * | 3/1995  | Goodin       | 604/103.07|
| 5,645,559 | A |   | 7/1997  | Hachtman et al. |        |
| 5,855,565 | A |   | 1/1999  | Bar-Cohen et al. |       |
| 5,925,060 | A |   | 7/1999  | Forber       |           |
| 6,066,149 | A | * | 5/2000  | Samson et al. | 606/159  |
| 6,123,715 | A |   | 9/2000  | Amplatz      |           |
| 6,156,064 | A | * | 12/2000 | Chouinard    | 623/1.44  |
| 6,336,934 | B1|   | 1/2002  | Gilson       |           |
| 6,544,276 | B1|   | 4/2003  | Azizi        |           |
| 6,579,306 | B1| * | 6/2003  | Voelker et al. | 623/1.11|
| 6,613,037 | B2| * | 9/2003  | Khosravi et al. | 604/507|
| 6,726,674 | B2| * | 4/2004  | Leu          | 604/101.01|
| 2001/0044647 | A1 | * | 11/2001 | Pinchuk et al. | 623/1.13 |

FOREIGN PATENT DOCUMENTS

| EP | 0791332     | 8/1997  |
| EP | 1360942     | 11/2003 |
| WO | WO 99/35975 | 7/1999  |
| WO | WO 01/72367 | 10/2001 |

\* cited by examiner

*Primary Examiner*—Nicholas D Lucchesi
*Assistant Examiner*—Laura A Bouchelle

(57) ABSTRACT

The device utilizes a reversibly expandable body partially covered by a blood impermeable sleeve. The device has a low profile collapsed state for delivery and a expanded state for deployment. The impermeable sleeve extends from a proximal portion to a distal portion of the expandable body and generally follows the contour of the expandable body. When deployed, the device is configured in the expanded state and has a generally hourglass, or dumbbell shape. In the expanded state, portions of the sleeve adjacent to the proximal and distal portions are placed in apposition to a vessel wall and blood is free to flow through the expandable body via inlets and outlets provided in the proximal and distal portions. As a result, an isolated treatment space is created that surrounds the device between the vessel wall and the blood impermeable sleeve adjacent to the neck portion of the expandable body.

21 Claims, 10 Drawing Sheets

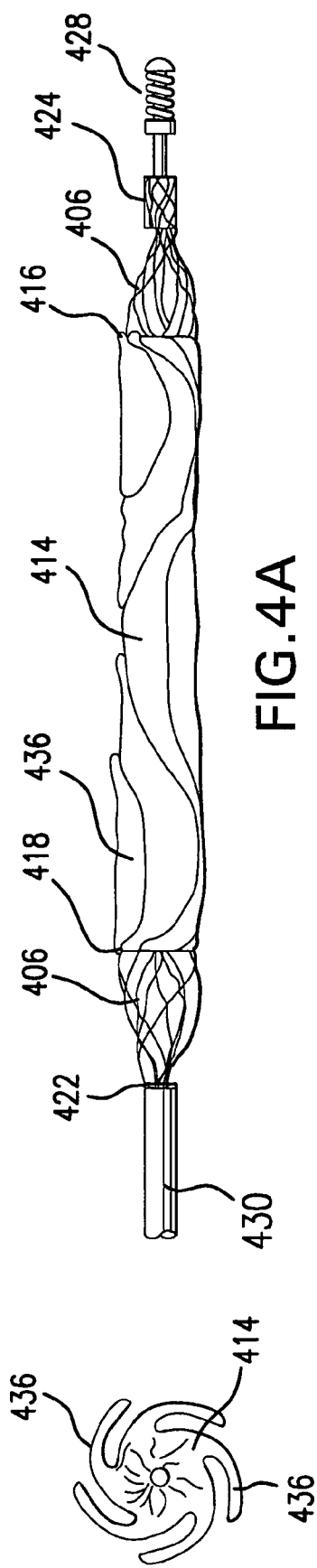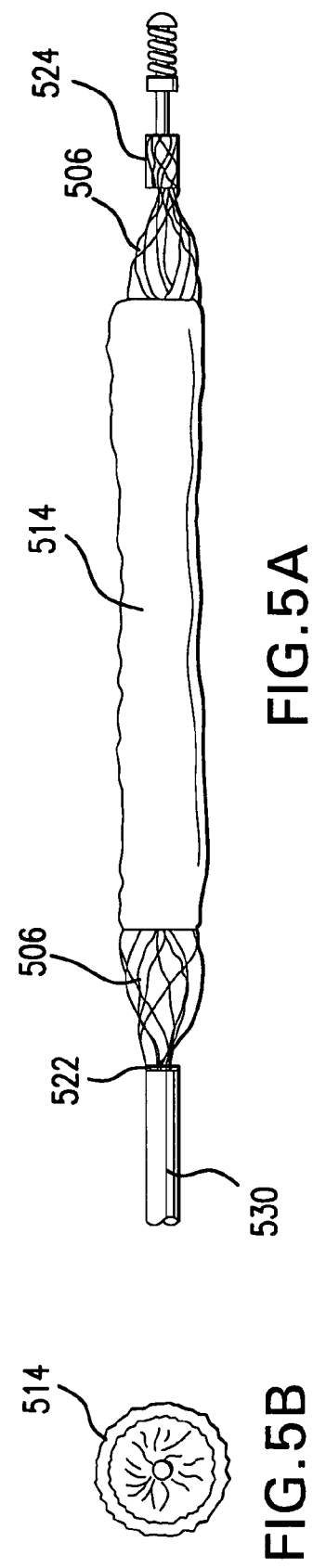

VESSEL ISOLATION DEVICE

FIELD OF THE INVENTION

The present invention relates to devices used for the treatment of vascular abnormalities. In particular, the present invention relates to devices used to isolate a portion of a vessel for localized treatment of that portion of the vessel.

BACKGROUND OF THE INVENTION

There are many different vascular abnormalities that require medical treatment. One of the more commonly treated abnormalities is a vascular aneurysm. Vascular aneurysms are abnormal enlargements of a blood vessel that may result from disease or genetic predisposition. Aneurysms may occur in any blood vessel, but many of them occur in the abdominal aorta. If left untreated, aneurysms may rupture leading to almost certain fatality.

Aneurysms are commonly treated by either bypassing the affected portion or filling the aneurysm. A bypass procedure involves the implantation of an artificial vascular graft with one end upstream of the aneurysm and a second end downstream of the aneurysm. After the graft is implanted, the blood flow bypasses the aneurysm by flowing through the graft. Alternatively, a device or substance may be injected into the aneurysm to permanently fill it.

A major disadvantage of conventional treatments for aneurysms has been that the blood flow through the affected vessel had to be blocked in order to perform the treatments efficiently. In the case of bypass surgery, the blood flow must be blocked upstream of the location where the upstream end of the graft will be implanted to avoid excessive blood loss. Where the treatment involves the implantation of a device within the aneurysm, the blood flow must be blocked upstream of the aneurysm so that the device may be placed properly. Similarly, where a substance is injected into certain forms of aneurysms (e.g., fusiform aneurysms) it may be necessary to block the blood flow upstream of the aneurysm so that the substance is not swept away during injection.

An arterial stenosis is another vascular abnormality that is commonly treated. A stenosis is a constriction of a vessel that may be created by formations of material deposits on the wall of a vessel or by thickening of the vessel wall itself. Such a narrowing of a vessel limits the amount of oxygenated blood reaching downstream organs and may trigger other medical conditions such as heart attacks.

Various treatments have also been developed to treat stenoses. The treatments typically rely on either surgical intervention or catheter-based therapies. One such surgical procedure for treating material formations is percutaneous transluminal coronary angioplasty, commonly referred to as "angioplasty" or "PTCA". The objective in angioplasty is to enlarge the lumen of the affected coronary artery by radial hydraulic expansion. PTCA is performed by inflating a balloon on a balloon catheter within the narrowed region of the vessel. Depending on the characteristics of the particular formation, it may be compressed or cracked and split by the inflated balloon. Alternatively, a dissolution agent may be applied to a material formation to cause the formation to dissolve and disengage the vessel wall. Unfortunately, the treatments for stenoses often suffer from problems similar to those associated with the treatment of aneurysms.

Isolation devices have been created to remedy some of the problems associated with the treatment of vascular abnormalities. Those devices have typically utilized a central body with a series of balloons disposed about the body. In order to inflate the balloons, at least one lumen was extended from a fluid source and through the central body to the balloons. The inflated balloons were used to completely isolate an annular volume between the balloons, the exterior surface of the central body and the vessel wall from the flow of blood. Oftentimes, small openings through the wall of the central body, located upstream of the balloons, allowed a limited amount of blood to enter and flow through a small central lumen in the body past the balloons and isolated volume.

Those isolation devices presented many disadvantages. First, the reliance on balloons as the sealing mechanism required that additional hardware be connected to the catheter outside of the patient's body, which makes it more cumbersome to make and use a small catheter. Second, catheters relying on balloons requires additional care to assure fluid tight seals are created during manufacture. In addition, balloon catheters pose a risk of fluid leakage from the balloon during use resulting in the loss of the seal between the balloon and the vessel wall. Finally, balloon devices are typically not self-expanding.

A need exists for a device that efficiently isolates a space within a vessel from the flow of blood, while allowing blood to flow past the isolated space, that is more reliable, more convenient to use, and easier to manufacture.

SUMMARY OF THE INVENTION

The present invention is a vessel isolation device that addresses the shortfalls of existing devices and efficiently isolates a space within a vessel from the flow of blood while allowing blood to flow past. The vessel isolation device is constructed from a reversibly expandable body that is partially covered by a blood impermeable sleeve.

Due to the reversibly expandable body, the device may be selectively transformed from a collapsed state to an expanded state or vice-versa. In the collapsed state, the device has a low profile to allow its delivery to an affected vascular region. When the device is in the expanded state (i.e., when the device is deployed), the expandable body generally takes the shape of an hourglass, or dumbbell, having both a proximal and distal portion each expanded radially larger than a central neck portion. The expandable body also includes at least one inlet on the proximal portion and at least one outlet on the distal portion so that blood may pass through the expandable body when it is in the expanded state.

The blood impermeable sleeve spans the distance between the proximal and distal portions. The sleeve is placed in apposition with the vessel wall adjacent to the proximal and distal portions when the device is in the expanded state. The sleeve generally follows the contour of the expandable body and as a result, a treatment space is created between the sleeve and vessel wall adjacent to the neck portion. As a result of the contact of the sleeve with the vessel wall, the treatment space is completely isolated from the flow of blood.

Isolation of the vessel wall is beneficial in many procedures. For example, during bypass surgery, a graft may be installed on the lumen using a conventional technique while the device allows blood to continue to flow through the lumen and simultaneously limits the blood loss during the procedure. Alternative procedures that may also benefit from the isolation of a portion of a vessel wall include treatment of aneurysms by installing occlusion devices or delivering substances such as cyanoacrylate, PTCA procedures, the application of a therapeutic agents to stenoses, or the application of gene therapy to a vessel wall. Since the treatment site may be isolated from the flow of blood, the problems associated with the influence of blood flow during the procedure are avoided.

A further advantage of the present invention arises from the use of an expansion mechanism other than inflation of a balloon with a fluid. The present invention does not require an inflation lumen so the central lumen may allow more blood to flow through the device. Furthermore, blood is not forced through small orifices of a rigid tube, as in other devices.

In addition, the present invention may employ a self-expanding body. The self-expanding body would require less handling than a device biased to a collapsed configuration in order to maintain proper deployment. Since the device would maintain itself in the expanded state, it would only require manipulation during the initial deployment and at the time of retraction.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

BRIEF DESCRIPTION OF THE DRAWINGS

These and other features, aspects and advantages of the present invention will become better understood with reference to the following description, appended claims, and accompanying drawings where:

FIGS. 4A-4B illustrate one embodiment of the vessel isolation device in a collapsed state with FIG. 4B being an end view of the vessel isolation device of FIG. 4A.

FIGS. 5A-5B illustrate an alternative embodiment of the vessel isolation device in a collapsed state with FIG. 5B being an end view of the vessel isolation device of FIG. 5A.

The accompanying drawings are not drawn to scale.

DETAILED DESCRIPTION OF THE INVENTION

The present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Figure 1:
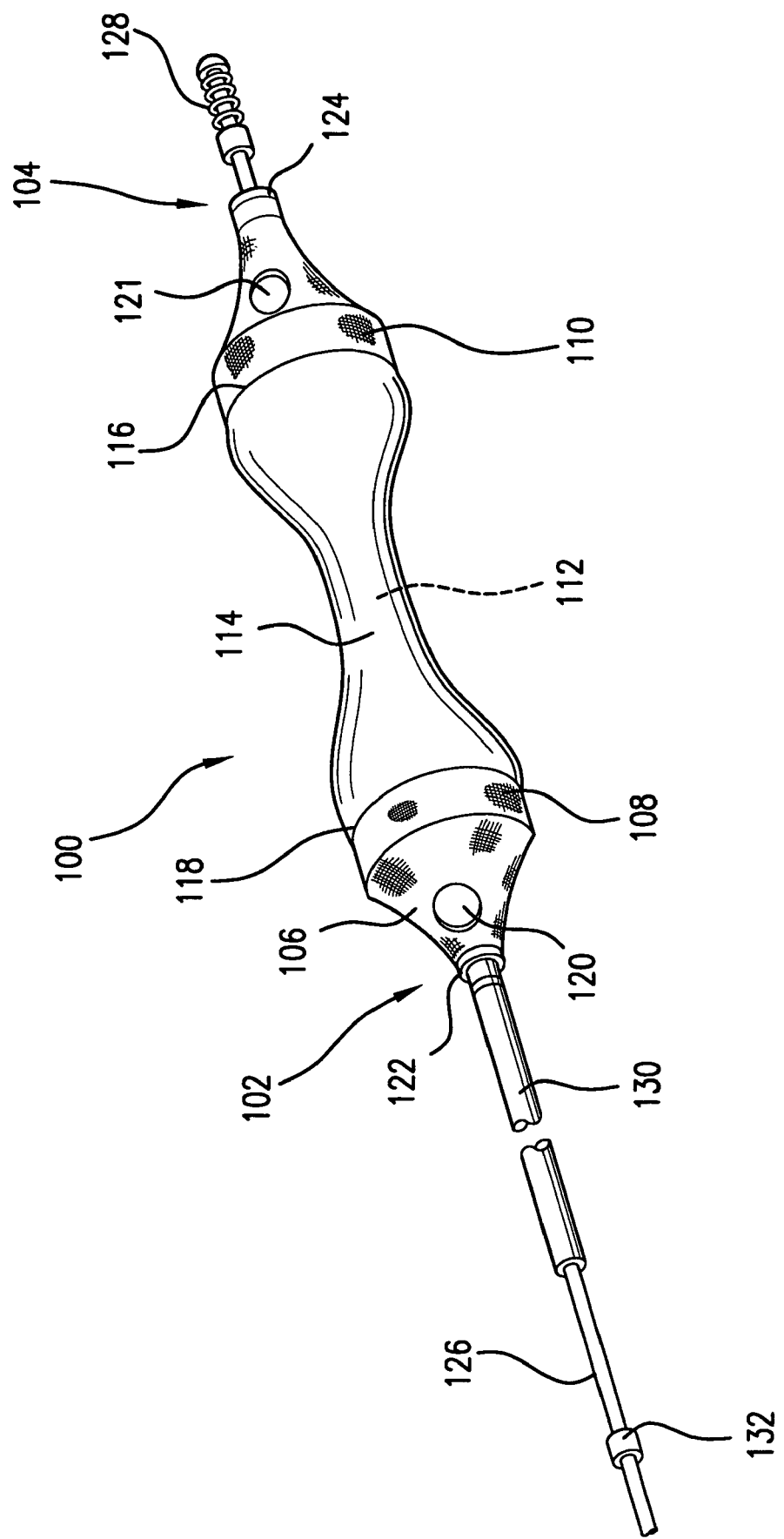
FIG. 1 is an isometric view of a vessel isolation device constructed on a guidewire platform and shown in an expanded state.

As shown in the exemplary embodiment of FIG. 1, the present invention includes a generally tubular vessel isolation device, indicated generally by reference numeral 100, mounted upon a delivery means, a guidewire 126 in the illustrated embodiment. It shall be understood that the delivery means is not limited to a guidewire. For example, a catheter tube may be used as a delivery means as discussed in detail below. Vessel isolation device 100 is generally constructed from a reversibly expandable body 106, and a blood impermeable sleeve 114. Vessel isolation device 100 is mounted on a delivery means and based on the delivery means used, an appropriate deployment means is included. After vessel isolation device 100 is delivered to the desired treatment site and deployed, it isolates a region of the vessel wall from flow of blood without occluding the flow through the vessel.

Figure 2:
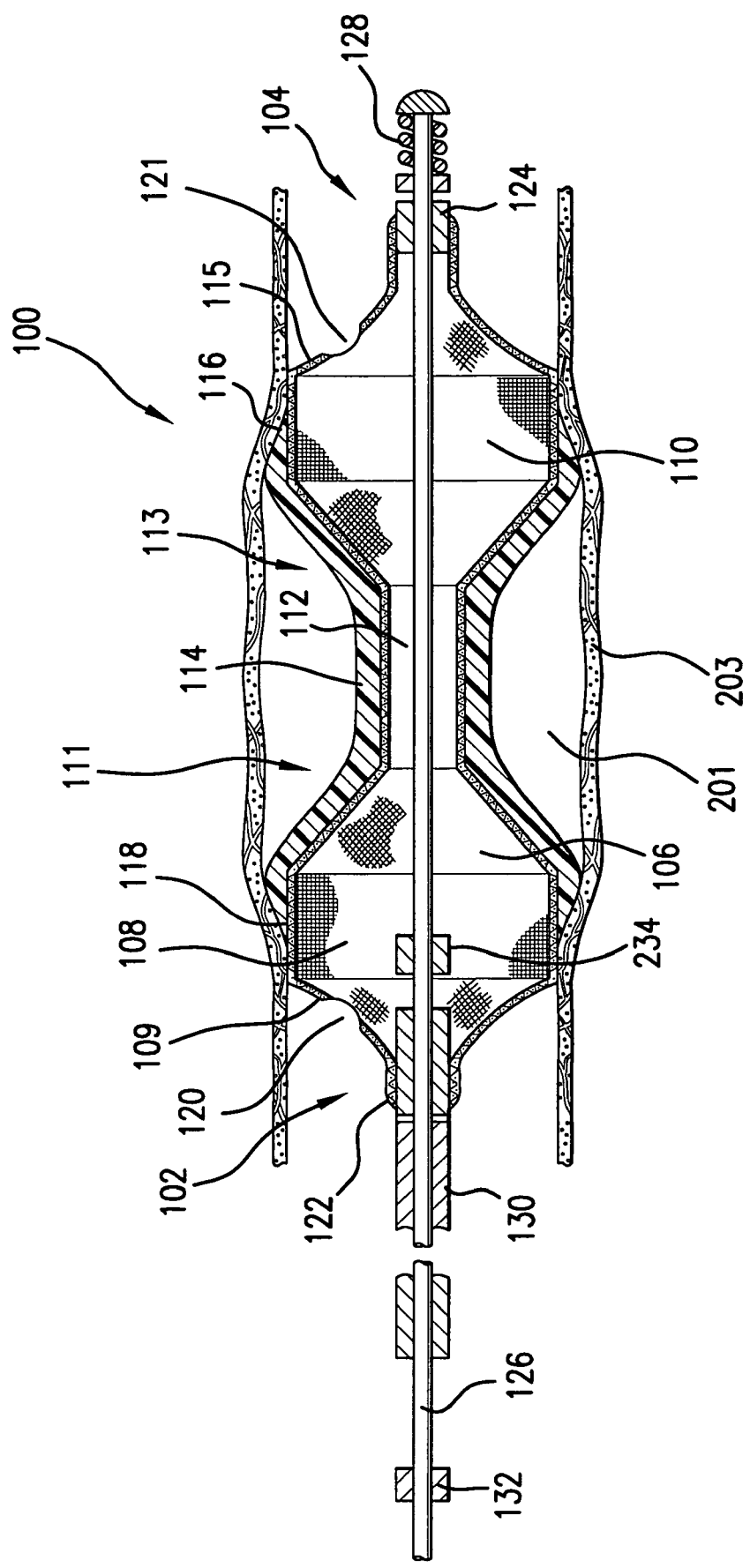
FIG. 2 is a longitudinal cross-sectional view of the vessel isolation device and deployment means of FIG. 1 shown in a patient's vessel.

A first embodiment of expandable body 106, shown in FIG. 2, generally includes a proximal portion 108, a distal portion 110, and a neck portion 112. Expandable body 106 may be selectively transformed between an expanded state and a collapsed state. In the expanded state shown in FIG. 2, proximal portion 108 and distal portion 110 each have outer diameters larger than the outer diameter of neck portion 112 giving expandable body 106 a generally hourglass, or dumbbell, shape. As used herein, diameter is used to describe the major transverse dimension of a particular portion of the body and it should be understood that the term is not meant to limit the invention to bodies having a circular cross-section.

As shown in FIG. 2, proximal portion 108 and distal portion 110 may have similar shapes. Expandable body 106 extends from a proximal end both distally and radially outward to form a proximal tapered surface 109 that extends to the outer diameter of proximal portion 108. In the embodiment of FIG. 2, proximal portion 108 extends at a constant outer diameter from proximal tapered surface 109 toward neck portion 112. Then at a distal end 111 of proximal portion 108, expandable body 106 tapers both distally and radially inward toward neck portion 112.

When the device is expanded within a vessel, it creates an isolated treatment space 201 and the size and shape of isolated treatment space 201 is generally defined by the inner surface of vessel wall 203 and the shape of vessel isolation device 100. As is apparent from FIG. 2, the expanded size of neck portion 112 closely correlates to the size of isolated treatment space 201. Therefore, the size of neck portion 112 may be selected to assure that the isolated treatment space 201 is sufficient for a particular procedure while still allowing blood to flow through the device. For example, the length of neck portion 112 may be increased or decreased to adjust the length of isolated treatment space 201, or the outer diameter of neck portion 112 may be increased or decreased to change the radial dimension of isolated treatment space 201.

At a distal end 113 of neck portion 112, expandable body tapers radially outward in the distal direction to the outer diameter of distal portion 110. Similar to proximal portion 108, distal portion 110 may extend distally at a constant outer diameter to the proximal end of distal tapered surface 115. Distal tapered surface 115 extends radially inward in the distal direction to a distal end 104 of expandable body 106.

The expandable body may terminate at a collar at either or both ends to connect the vessel isolation device to a delivery means. In the embodiment shown in FIG. 2, expandable body 106 terminates at a collar at each end and the delivery means is a guidewire 126 having a flexible distal tip 128. In that embodiment, proximal and distal collars 122 and 124 are non-expanding, tubular members that are mounted on guidewire 126 and coupled to expandable body 106 at its proximal and distal ends 102 and 104. Alternatively, the ends of the expandable body may be soldered directly to a guidewire or terminated independently. For example, where a slidable connection between the expandable body and a guidewire is desired, the ends of the filaments in a braided material, or the ends of the struts, may be soldered together to form an integral collar that is slidably coupled to the guidewire.

In order to allow blood to flow through expandable body 106, inlets 120 are provided through proximal tapered surface 109 of proximal portion 108 and outlets 121 are provided through distal tapered surface 115 of the distal portion 110. Inlets 120 are in fluid communication with outlets 121 such that blood flowing into inlets 120 on proximal portion 108 can flow through expandable body 106 in its expanded state and out through outlets 121 on distal portion 110.

The construction of expandable body 106 may take various forms. In one embodiment, expandable body 106 is formed of a braided material. For example, the braided material may be formed with nitinol filaments and those filaments may be drawn binary nitinol alloy wires or wires made by a drawn filled tubing (DFT) process, in which a non-nitinol core, such as platinum, is encased in nitinol. The braided material may also be made from other metals that may include ELGILOY® metal available from Fort Wayne Metals of Elgin, Ill.; stainless steel; cobalt-based alloys (e.g., MP35N); or biocompatible polymers. Expandable body 106 is preferably formed and heat treated in its expanded state so that it has a tendency to return to that state. Alternatively, expandable body 106 may be a frame constructed from a series of struts. The struts may also be made of nitinol; other metals which may include ELGILOY® metal available from Fort Wayne Metals of Elgin, Ill.; stainless steel; cobalt-based alloys (e.g., MP35N); or biocompatible polymers.

Sleeve 114 provides a blood impermeable surface for vessel isolation device 100. Sleeve 114 is generally tubular and terminates at a proximal end 118 and a distal end 116. Expandable body 106 extends through sleeve 114 so that proximal end 118 is located adjacent to proximal portion 108 and distal end 116 is located adjacent to distal portion 110. Sleeve 114 and expandable body 106 are fixedly coupled at proximal portion 108 and distal portion 110 and sleeve 114 is constructed to generally follow the contour of expandable body 106 in both the collapsed and expanded states. Sleeve 114 may be coupled to expandable body 106 by suturing, applying biocompatible adhesives, heat welding the sleeve 114 to an inner retention band through voids in the expandable body, or any other technique known in the art.

Proximal end 118 and distal end 116 are located on expandable body 106 so that at least a portion of sleeve 114 extends to or beyond the location on the proximal and distal portions 108 and 110 having the largest outer diameters. This configuration ensures that when vessel isolation device 100 is expanded within a patient's vessel both a proximal and distal portion of sleeve 114 are placed in apposition to the inner surface of the vessel wall 203 creating isolated treatment space 201.

Figure 3:
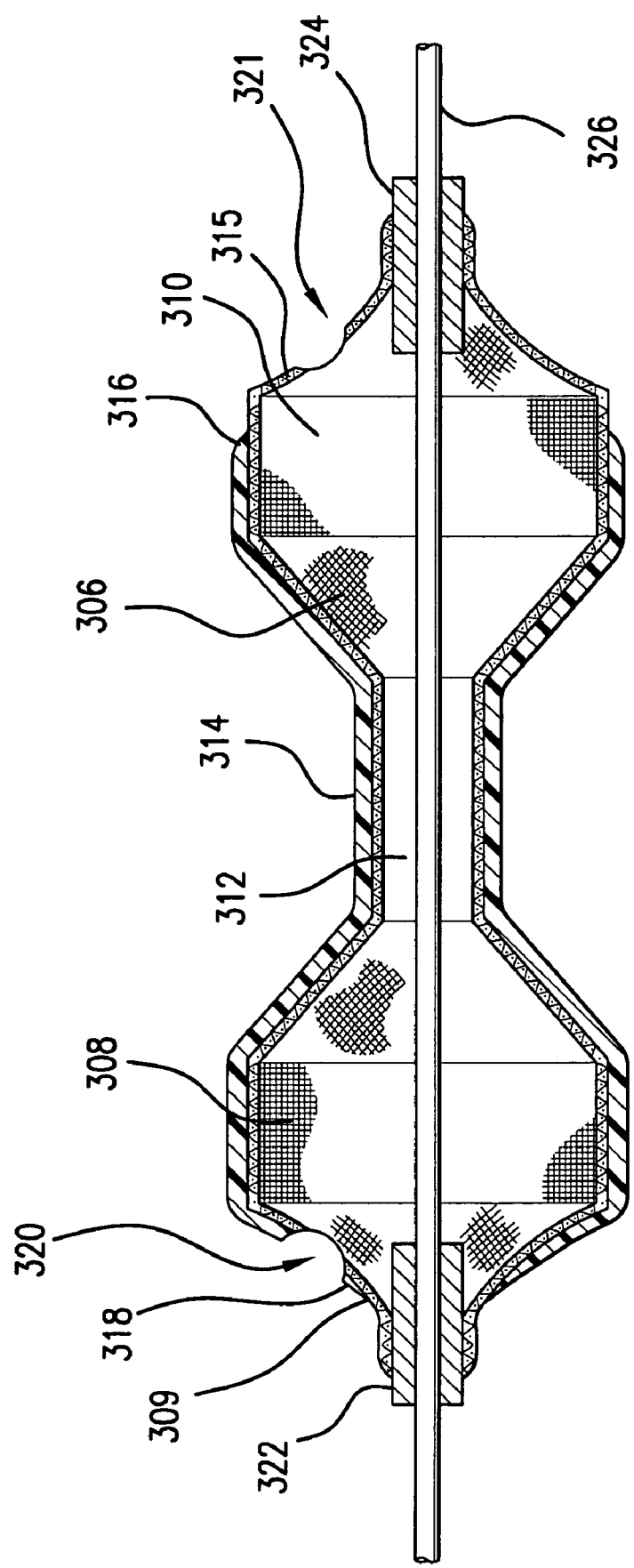
FIG. 3 is a longitudinal cross-sectional view of an additional embodiment of the vessel isolation device of FIG. 1.

As shown in the embodiment of FIG. 3, proximal end 318 may extend past the major dimension of the proximal portion 308 and onto the proximal tapered surface 309. Although it is not shown, it shall be understood that distal end 316 may extend onto distal tapered surface 315 in addition to or as an alternative to proximal end 318. If sleeve 314 extends onto either of the tapered surfaces, it should be understood that it should not interfere with inlets 320 or outlets 321 so that blood is free to flow into and out of vessel isolation device 300.

In the collapsed state, vessel isolation device 100 maintains a low profile. In that state, vessel isolation device 100 is generally cylindrical in shape and has a generally uniform outer diameter over its length with sleeve 114 collapsed upon expandable body 106. FIGS. 4A-4B show the collapsed state of a vessel isolation device utilizing an inelastic material for sleeve 414.

Various inelastic and elastic materials are appropriate for sleeve 414. Sleeve 414 may be made from inelastic materials commonly used for stent graphs which may include polytetrafluoroethylene (PTFE) such as GORE-TEX® expanded PTFE (a registered trademark of W.L. Gore & Associates, Inc.), thermoplastics, DACRON® polyester fabric (a registered trademark of E.I. du Pont de Nemours and Company, Inc.). Also suitable are inelastic materials commonly used for dilatation balloons which may include nylons, polyvinylchloride, and polyethylene such as polyethylene terephthalate. Alternatively, as shown in FIGS. 5A-5B, a sleeve 514 may be constructed from an elastic material. Elastic materials that may be used for sleeve 514 include natural rubbers, silicone rubbers, latex rubbers, thermoplastic elastomers, polyurethane elastomers, or PEBAX® polyethylene block amide copolymer (a registered trademark of Ato Chimie, Inc.).

Various techniques are known in the art for creating a collapsible sleeve 414 from those materials. One method of maintaining the lower profile with an inelastic material is to create sleeve 414 with pre-formed biased folds, as shown in FIGS. 4A-4B. Those pre-formed biased folds assure that when expandable body 406 is in the collapsed state, sleeve 414 material has a natural tendency to form folds 436 and wrap around expandable body 406.

One such method of creating pre-formed biased folds with PEBAX® polyethylene block amide copolymer is disclosed in U.S. Pat. No. 5,350,361, the disclosure of which is incorporated by reference in its entirety herein. That method includes drawing a balloon into a channel of a folding jig, where the channel is defined by three adjacent cylindrical pins forcing the balloon to have a generally triangular cross section. Once inserted, suction is applied to the inflation lumen of the balloon causing it to collapse upon itself creating three flaps. While the suction is maintained, the collapsed balloon is removed from the channel and heating elements are applied between each of the flaps to soften the balloon material. The softened material creates three longitudinal creases in the balloon which help to ensure that the balloon repetitively collapses in the symmetrical three-fold configuration.

Another technique for forming folds involves folding the balloon as described above using a folding jig and applying shrink tubing over the folded balloon to temporarily hold the sleeve material in the desired folded configuration. The balloon is then heat set, and the shrink tubing is removed. The combination of pressure and heating can cause the sleeve material to retain the folded configuration.

In order to create an elastic sleeve 514, a selected portion of expandable body 506 may be dip coated in the sleeve material. It is preferable that expandable body 506 be dip coated in the elastic material while expandable body 506 is in an expanded state so that sleeve 514 is biased to the expanded state to assist deployment. Alternatively, sleeve 514 may be constructed separately and subsequently mounted on expandable body 506 as previously described.

Deployment means are provided to control the transformation between the collapsed and expanded states of vessel isolation device 100. As shown in FIG. 2, vessel isolation device 100 may be constructed on a guidewire platform utilizing a deployment control member 130, which is slidably attached to guidewire 126. In that embodiment, distal collar 124 is restricted from sliding longitudinally along guidewire 126. Deployment control member 130 is coupled to proximal collar 122, or alternatively may be substituted for proximal collar 122. A distal stop 234 is fixedly coupled to guidewire 126. Distal stop 234 limits the longitudinal travel of proximal collar 122 and deployment control member 130 in the distal direction. A proximal stop 132 may also be provided and fixedly coupled to guidewire 126 to limit the longitudinal travel of proximal collar 122 and deployment control member 130 in the proximal direction. In order to transform vessel isolation device 100 from the expanded to the collapsed state, proximal collar 122 and deployment control member 130 are slid proximally. As a result, expandable body 106 is elongated and the profile gradually reduces until vessel isolation device 100 reaches the collapsed state. Conversely, by sliding proximal collar 122 and deployment control member 130 distally, expandable body 106 is shortened and the profile gradually expands until vessel isolation device 100 reaches the expanded state.

Figure 6:
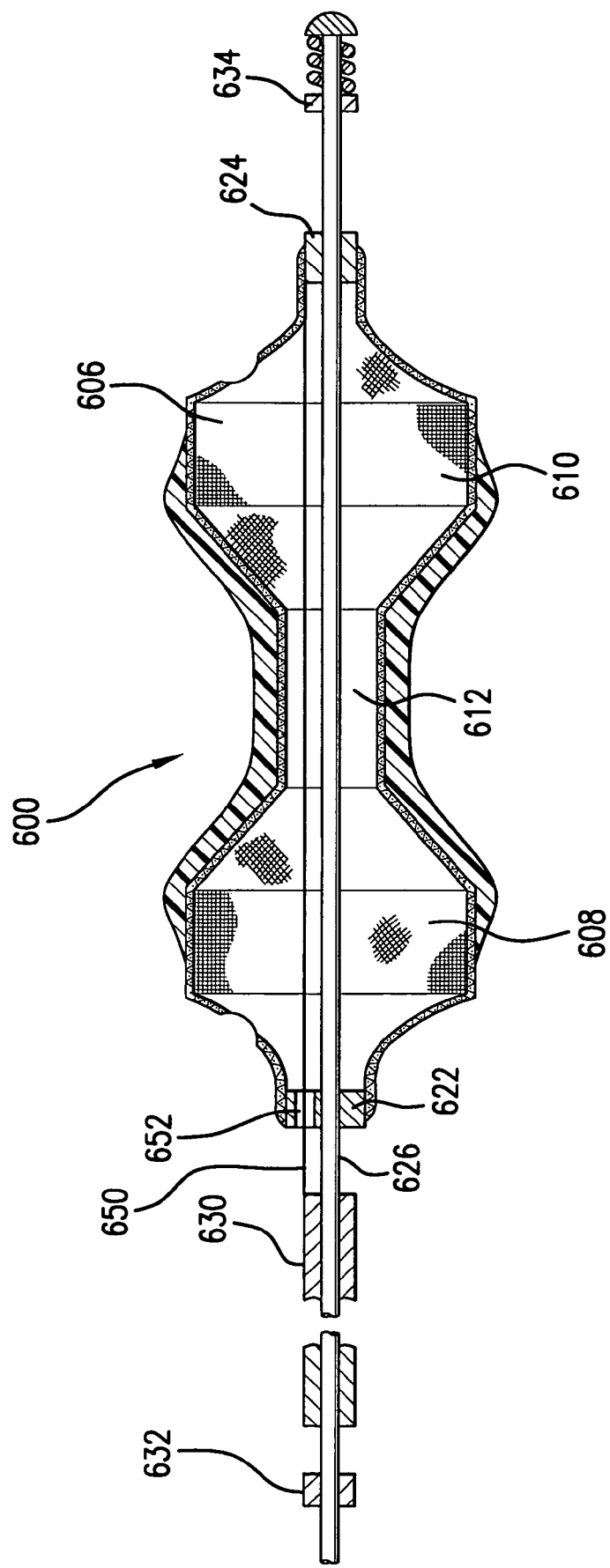
FIG. 6 is a longitudinal cross-sectional view of a still further embodiment of the vessel isolation device and deployment means of FIG. 1.

Alternatively, as shown in FIG. 6, deployment means may be configured such that vessel isolation device 600 reaches the collapsed state when deployment control member 630 is slid in the distal direction on guidewire 626. In that embodiment, the deployment means includes a deployment control member 630 slidably disposed about guidewire 626, a deployment link 650, proximal collar 622 and distal collar 624. In contrast to the deployment means shown in FIG. 2, deployment control member 630 is coupled to distal collar 624 by deployment link 650, and proximal collar 622 is restricted from longitudinally sliding along guidewire 626. In this embodiment, a throughway 652 is provided through proximal collar 622 allowing deployment link 650 to extend through expandable body 606 to distal collar 624. When it is desired to transform vessel isolation device 600 into the collapsed state, deployment control member 630 is slid distally along guidewire 626. As deployment control member 630 is slid distally, it forces deployment link 650 to slide further distal through proximal collar 622. The advancement of deployment link 650 causes distal collar to move further distal resulting in the elongation and collapse of expandable body 606. A proximal stop 632 and a distal stop 634 are provided to restrict the range of movement of deployment control member 630 during the expansion and retraction of vessel isolation device 600.

Figure 7:
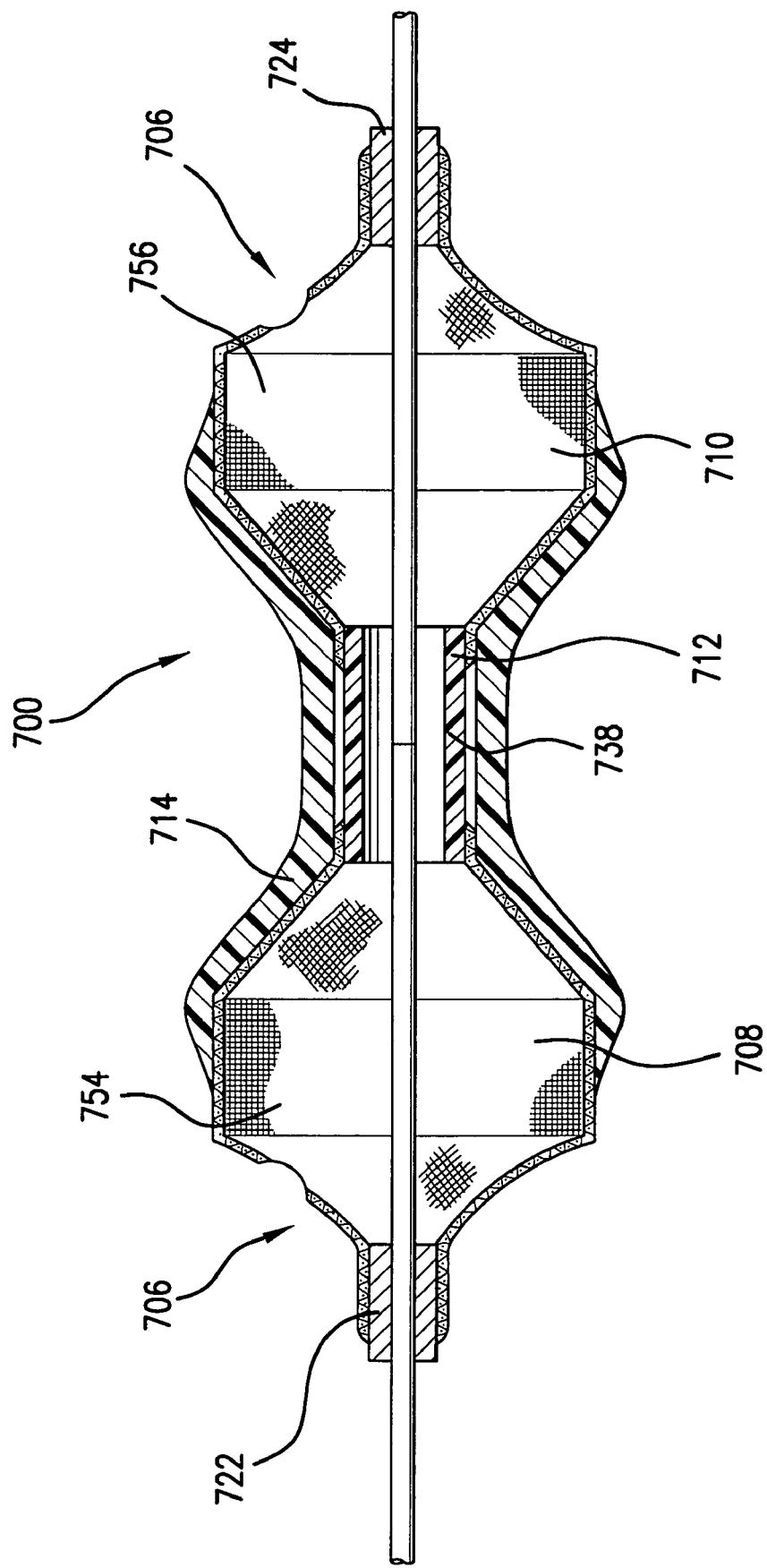
FIG. 7 is a longitudinal cross-sectional view of a further embodiment of the vessel isolation device of FIG. 1.

An alternative embodiment of a vessel isolation device 700 is shown in FIG. 7. In that embodiment, vessel isolation device 700 utilizes a modular expandable body 706. Expandable body 706 is constructed by combining a proximal member 754, a distal member 756 and a neck member 738. When those components are combined, proximal member 754 forms proximal portion 708, distal member 756 forms distal portion 710 and neck member 738 forms neck portion 712 of expandable body 706.

In the embodiment of FIG. 7, proximal member 754 and distal member 756 are constructed from a braided material similar to expandable body 106 of FIG. 1. Like the previous embodiment, the braided material may be made of drawn binary nitinol alloy filaments, nitinol filaments made by a DFT process, or any other biocompatible filaments. Each of proximal member 754 and distal member 756 is formed so that it has a tendency to return to the expanded shape. Alternatively, each of proximal member 754 and distal member 756 may be a frame constructed from a series of struts. The struts may be made of nitinol, stainless steel, or any other biocompatible metallic or polymeric material.

Neck member 738 extends between proximal member 754 and distal member 756. Neck member 738 may be expandable or non-expandable and is sized such that it is large enough to permit sufficient blood flow therethrough when expanded vessel isolation device 700 is deployed and small enough to navigate the patient's vasculature when vessel isolation device 700 is collapsed.

Neck member 738 may be attached to proximal member 754 and distal member 756 by various processes and the method of combination may be tailored to the materials employed for the members. Brazing, soldering, adhesive bonding, and suturing are all methods of combination that may be used. In embodiments utilizing metallic parts, brazing, adhesive bonding or soldering may be most effective. In embodiments that combine metallic with non-metallic parts, it may be most effective to use adhesive bonding (e.g., adhesive bands, etc.).

If neck member 738 is expandable, it may be made from of a braided material identical to those used for proximal member 754 and distal member 756. For example, the braided material may be constructed with drawn binary nitinol alloy filaments, nitinol filaments made by a DFT process, or any other biocompatible filaments. Alternatively, neck member 738 may be a frame constructed from a series of struts. The struts may be made of nitinol, stainless steel or any other biocompatible material having strength sufficient to support vessel isolation device 700 while being resilient enough to allow transformation of the vessel isolation device between the collapsed and expanded states.

Alternatively, where a non-expandable neck member 738 is used, it may be constructed from any biocompatible metal, polymer or woven fabric. If neck member 738 is metal, it may be of a portion of a metal hypotube. As a further alternative, neck member 738 may be constructed from polymer tubing which may be made from high-density polyethylene, polyimide, polyamides, polyolefins, PEBAX® polyethylene block amide copolymer, or any other biocompatible polymer. Where a woven fabric is desirable, neck member 738 may be made of DACRON® polyester fabric, GORE-TEX® expanded PTFE, or any other biocompatible woven material.

Figure 8A:
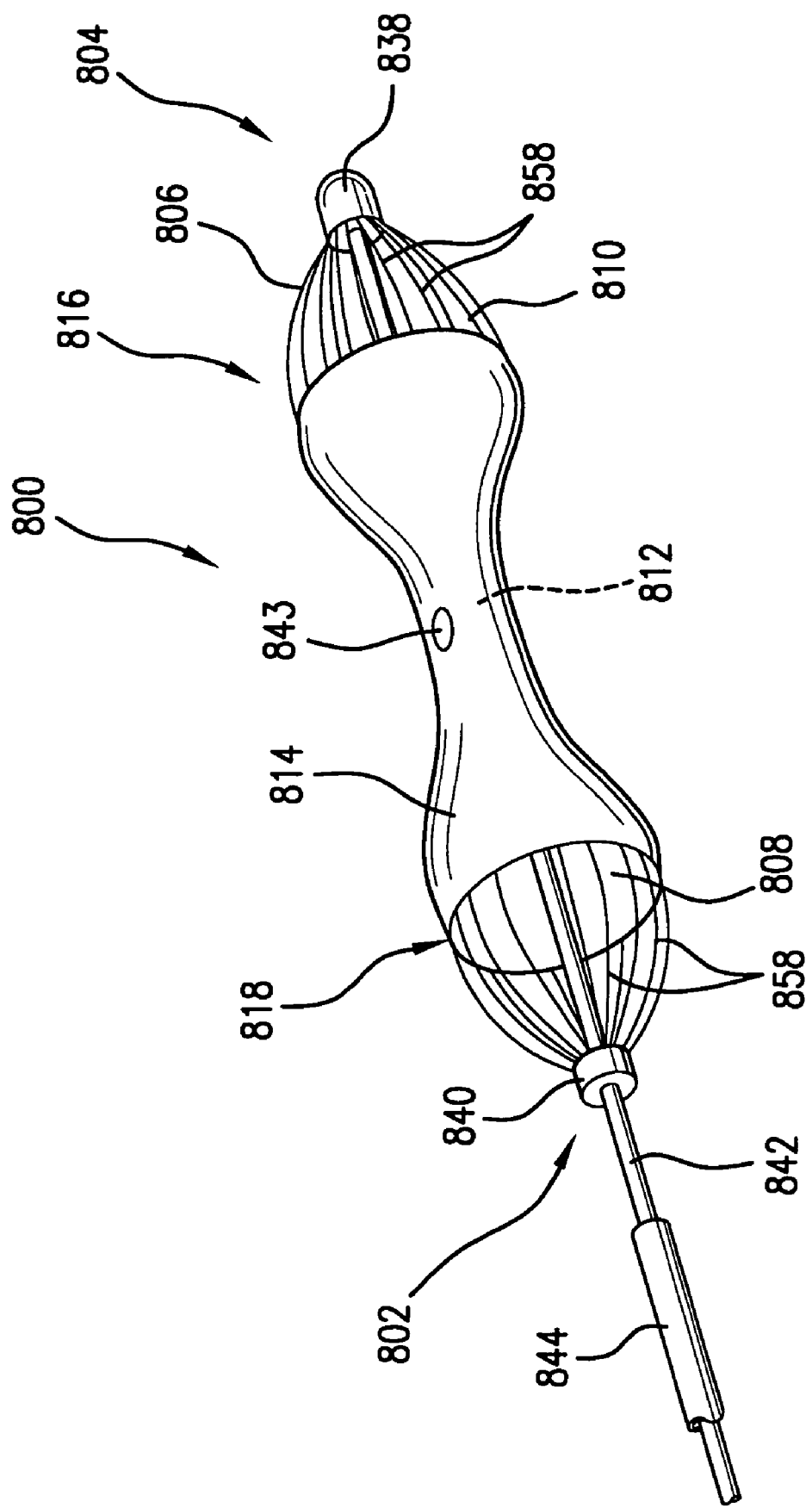
FIGS. 8A-8B show a further embodiment of the vessel isolation device and deployment means, with FIG. 8B being a longitudinal cross-sectional view of the vessel isolation device shown in the isometric view of FIG. 8A.
Figure 8B:
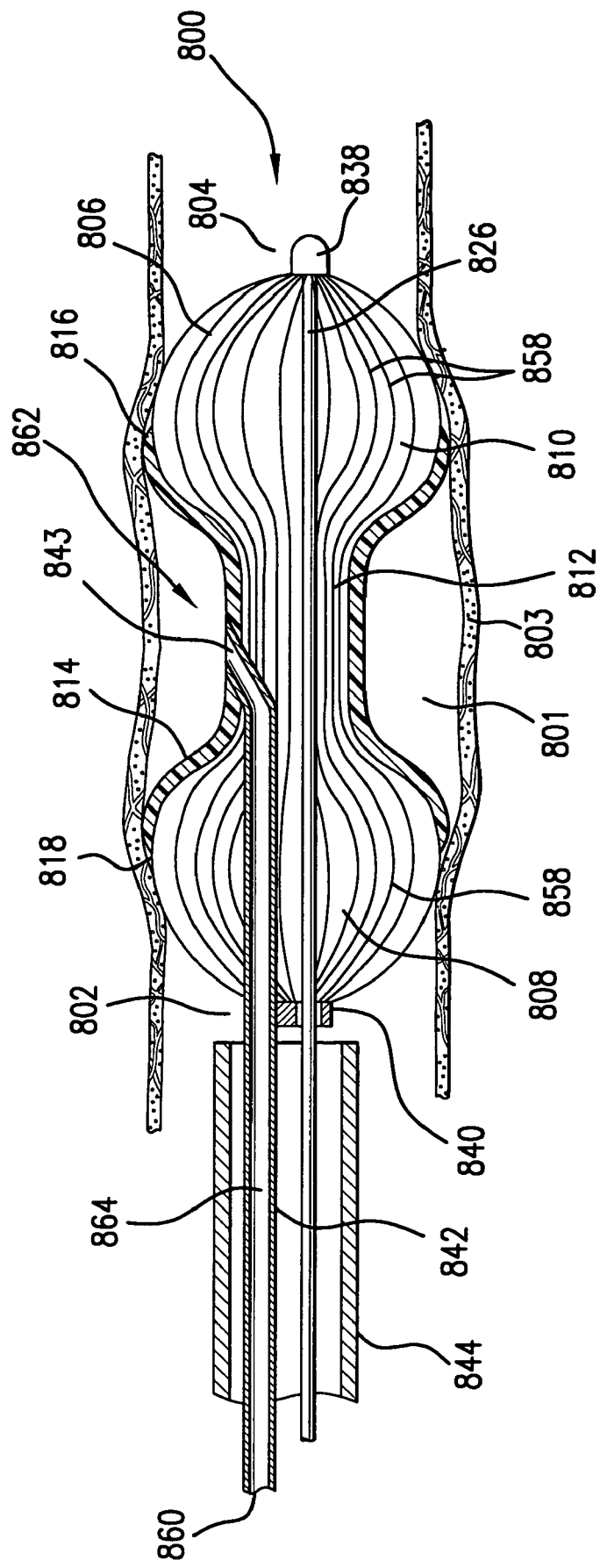

FIGS. 8A-8B illustrate a further embodiment of a vessel isolation device 800. Vessel isolation device 800 employs an expandable body 806 constructed of struts 858, sleeve 814, catheter tube 842, and deployment sheath 844.

Catheter tube 842 has a proximal end 860, a distal end 862 and defines an access lumen 864. It provides access to isolated treatment space 801 after vessel isolation device 800 is deployed. Catheter tube 842 passes through proximal end 802 of vessel isolation device 800 and is coupled to sleeve 814 so that access lumen 864 is in fluid communication with isolated treatment space 801 at access port 843. In this embodiment, catheter tube extends through the entire thickness of sleeve 814 and terminates flush with an outer surface of sleeve 814. Alternatively, catheter tube may terminate within the thickness of sleeve 814 or beyond the outer surface of sleeve 814 while still placing access lumen 864 in fluid communication with isolated treatment space 801.

Catheter tube 842 may be formed from any biocompatible metallic or polymeric material, for example stainless steel, polyethylene, polyimide, polyamides, polyolefins, or PEBAX® polyethylene block amide copolymer. In one embodiment, catheter tube 842 is made from high-density polyethylene due to its low friction characteristics. Catheter tube 842 may be extruded or formed in any other process known in the art for producing tubing used in medical devices.

Although guidewire 826 is shown in FIG. 8, catheter tube 842 may obviate the need for guidewire 826 since catheter tube 842 may be used in combination with a deployment sheath 844 to provide a sufficient deployment means. Deployment sheath 844 is sized to slidably receive vessel isolation device 800 in its collapsed state and catheter tube 842 can be used to move vessel isolation device 800 relative to deployment sheath 844. Prior to implantation, vessel isolation device 800 is loaded into deployment sheath 844. Deployment sheath 844, with the loaded vessel isolation device 800, can then be navigated to the desired implantation location. At that point, vessel isolation device 800 is urged out of deployment sheath 844 by sliding catheter tube 842 further distal through the deployment sheath 844.

As vessel isolation device 800 exits deployment sheath 844, the expanded bias of expandable body 806 causes vessel isolation device 800 to transform from the collapsed state into its expanded state. It shall be understood that guidewire 826 may be substituted for or used in combination with catheter tube 842. A combination of catheter tube 842 with guidewire 826 may help to deploy and retract vessel isolation device 800 while providing intravascular access to isolated treatment space 801.

Figure 9:
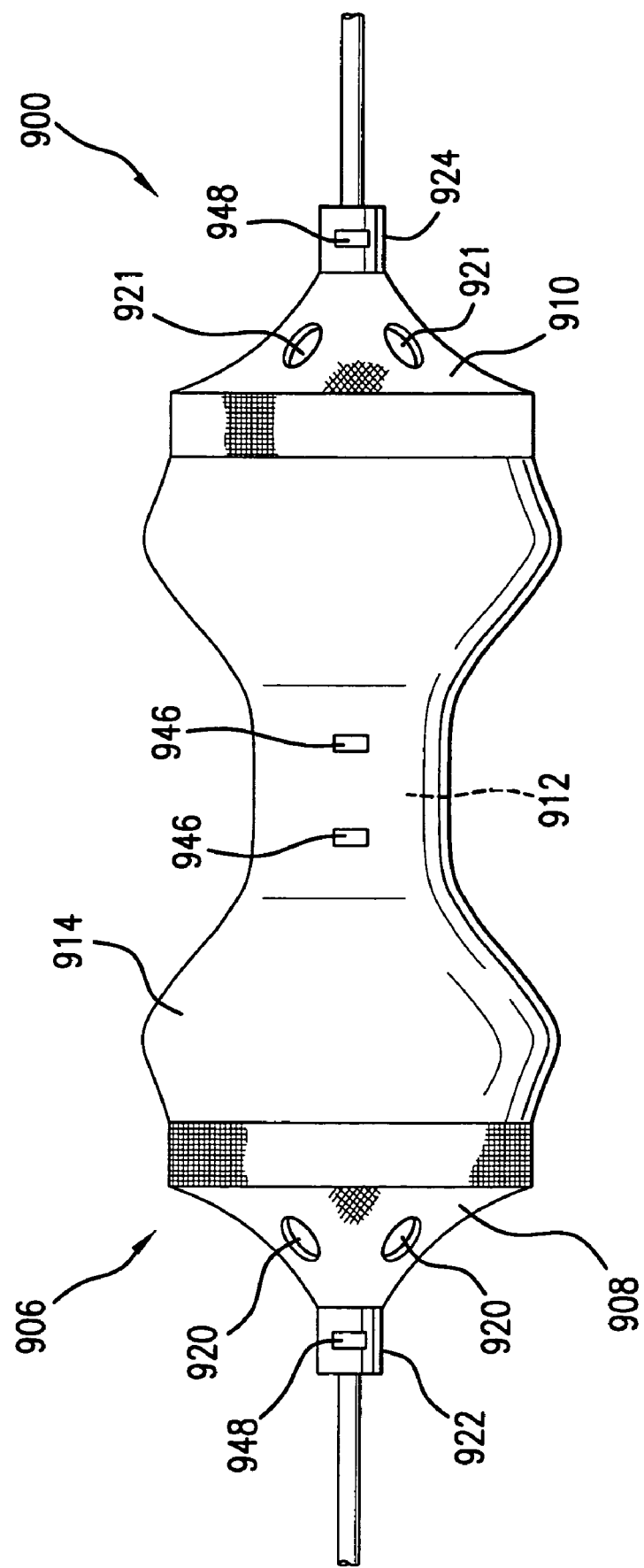
FIG. 9 illustrates additional alternative features of the vessel isolation device.

As a further alternative feature, a vessel isolation device 900 may include radiopaque markers 946 and 948, as shown in FIG. 9. Radiopaque markers may be included on proximal collar 922 and distal collar 924 so that a clinician can easily determine whether expandable body 906 is in the expanded or collapsed state by viewing the distance between the two markers. In addition, radiopaque markers 946 may be included on sleeve 914 in neck portion 912 so that vessel isolation device 900 may be easily positioned to isolate the desired vascular portion. It shall be understood that any number of radiopaque markers could be used to locate the vessel isolation device or to determine the state of the vessel isolation device. Alternatively, expandable body 906 may include radiopaque elements. For example, expandable body 906 can be made from DFT filaments, where the core is a radiopaque material such as a platinum alloy, or radiopaque filaments can be interwoven in a braided material. As a further alternative, where struts are used to form the expandable body, at least one strut may be constructed from a radiopaque material.

Multiple inlets 920 and outlets 921 may be provided through each of the proximal and distal portions, 908 and 910, to allow increased blood flow through vessel isolation device 900. Any number of inlets 920 and outlets 921 may be utilized.

Figure 10:
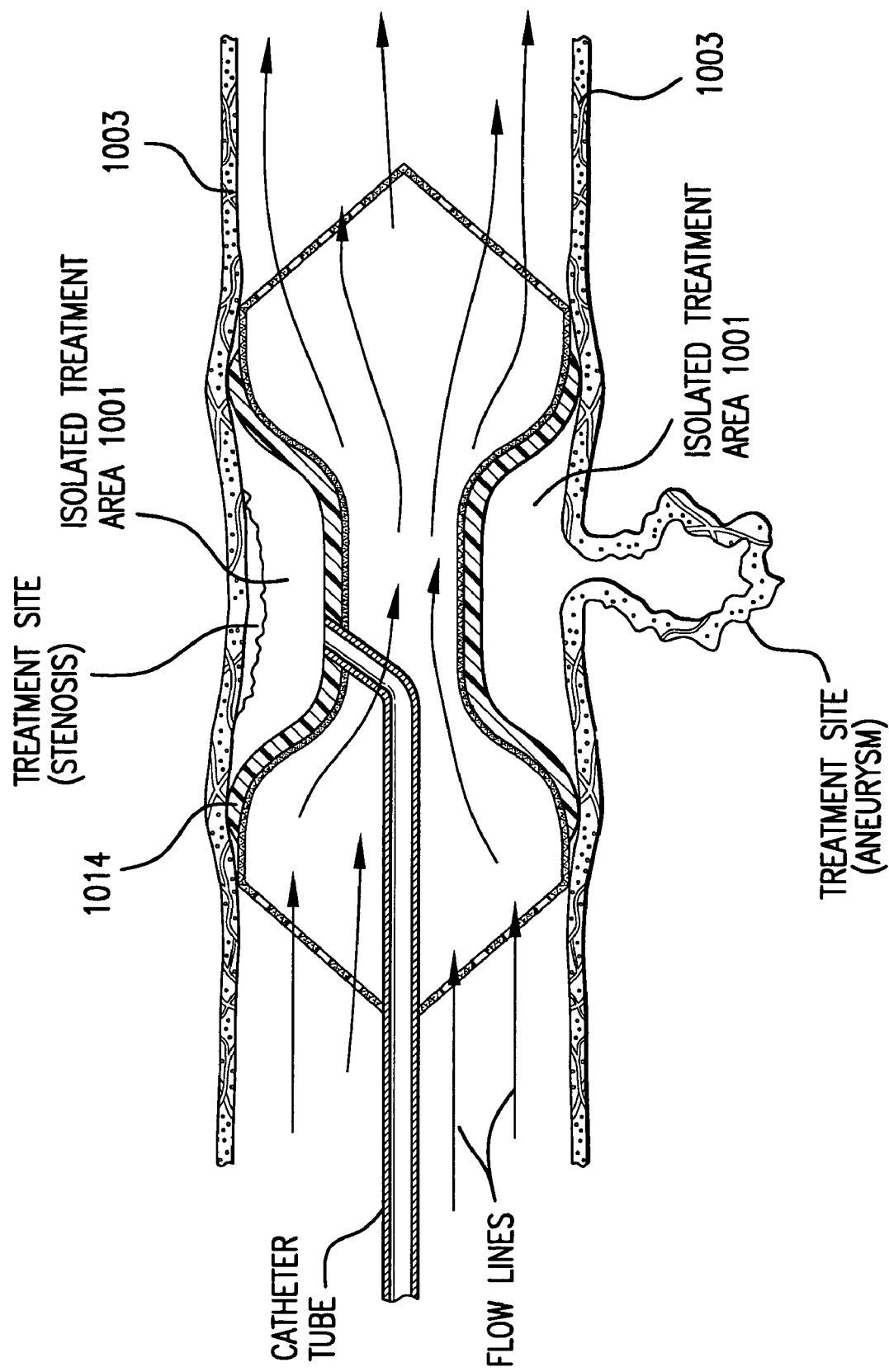
FIG. 10 illustrates the blood flow through a vessel isolation device located within a patient's vasculature.

In order to use the vessel isolation device, it is first transformed into the collapsed state. Once collapsed, the device is navigated through the vasculature to the treatment site by any one of many procedures well known in the art. If radiopaque markers, elements or struts are included, the device may be located in the proper position fluoroscopically. Once the device is located, it is deployed such that the distal portion is located distal of the treatment site and the proximal portion is located proximal of the treatment site. As a result, the proximal and distal portions will straddle the treatment site located in isolated treatment space 1001, as shown in FIG. 10. After deployment, portions of sleeve 1014 are located in apposition to the vessel wall adjacent to the proximal and distal portions thereby creating an isolated treatment space 1001. As shown by the flow lines in FIG. 10, the blood flow would be directed through the lumen defined by sleeve 1014 and the treatment site is isolated from that flow.

After the device is located, the desired procedure may be performed within the isolated treatment space. The appropriate embodiment of the vessel isolation device would be determined by the desired treatment. For example, where a bypass procedure is to be performed and the device is being used to reduce blood loss during graft implantation, any of the embodiments may be used. It would not be necessary in such a procedure to use an embodiment having a catheter tube. On the other hand, where the user wishes to inject a substance or a device into the isolated treatment space, without piercing the vessel wall, it would be desirable to use an embodiment including a catheter tube, such as the embodiment of FIGS. 8A-8B. Using such an embodiment allows access to the isolated treatment space from within the vessel. Where a dissolution agent is employed, the catheter tube may be used to first inject the agent and subsequently aspirate the agent and debris.

Once the procedure has been performed in the isolated treatment space, the device is transformed back to the collapsed state and removed from the vessel. After the vessel isolation device is transformed back to the collapsed state, blood is allowed to return to near normal flow through the vessel.

While this invention has been particularly shown and described with reference to preferred embodiments thereof, it will be understood by those skilled in the art that various changes in form and details may be made therein without departing from the spirit and scope of the invention.

What is claimed is:

1. A vessel isolation device, comprising:
a noninflatable expandable body, reversibly expandable from a low profile collapsed state to a generally hourglass-shaped expanded state, including
a proximal portion having at least one inlet formed therein,
a distal portion having at least one outlet formed therein, the outlet being in fluid communication with the inlet via a central lumen defined by the expandable body, and
a neck portion disposed between the proximal and distal portions; and
a blood impermeable sleeve disposed about the neck portion of the expandable body and at least a portion of the proximal and distal portions of the expandable body, the sleeve being reversibly expandable with the expandable body from the collapsed state to the expanded state,
wherein the sleeve is adapted to be placed in continuous circumferential contact with a vessel wall adjacent to the proximal portion and the distal portion when the expandable body is in the expanded state, thereby creating an isolated treatment space; and
wherein the isolation device further comprises at least one catheter tube having proximal and distal ends and an access lumen extending therebetween, wherein the catheter tube distal end is coupled to the blood impermeable sleeve such that the access lumen is in fluid communication with the isolated treatment space at an access port extending through the impermeable sleeve, the at least one catheter tube extending from the access port into the central lumen and protruding from the proximal portion of the expandable body adjacent the at least one inlet.

2. The vessel isolation device of claim 1, wherein the neck portion is expandable.

3. The vessel isolation device of claim 1, wherein the expandable body is formed of a braided structure.

4. The vessel isolation device of claim 1, wherein the expandable body is self-expanding.

5. The vessel isolation device of claim 4, wherein the expandable body is constructed of nitinol.

6. The vessel isolation device of claim 1, wherein the expandable body is constructed from a plurality of braided structures.

7. The vessel isolation device of claim 6, wherein the plurality of braided structures are interconnected by at least one neck element.

8. The vessel isolation device of claim 1, wherein the sleeve is an inelastic material.

9. The vessel isolation device of claim 8, wherein the material of the sleeve is selected from the group consisting of polyester and polytetrafluoroethylene.

10. The vessel isolation device of claim 1, wherein the sleeve is an elastic material.

11. The vessel isolation device of claim 10, wherein the sleeve is selected from the group consisting of natural rubber, silicone rubber, latex rubber, thermoplastic elastomer, and polyurethane elastomer.

12. The vessel isolation device of claim 1, further comprising:
a first radiopaque marker disposed on the distal portion; and
a second radiopaque marker disposed on the proximal portion.

13. The vessel isolation device of claim 1, further comprising: at least one radiopaque marker located on the neck portion.

14. The vessel isolation device of claim 1, further comprising:
a first radiopaque marker disposed on a distal end of the distal portion;
a second radiopaque marker disposed on a distal end of the neck portion;
a third radiopaque marker disposed on a proximal end of the neck portion; and
a fourth radiopaque marker disposed on a proximal end of the proximal portion.

15. A vessel isolation system, comprising
a noninflatable expandable body, reversibly expandable from a low profile collapsed state to a generally hourglass-shaped expanded state, including
a proximal portion having at least one inlet formed therein,
a distal portion having at least one outlet formed therein, the outlet being in fluid communication with the inlet via a central lumen defined by the expandable body, and
a neck portion disposed between the proximal and distal portions;
a blood impermeable sleeve disposed about the neck portion of the expandable body and at least a portion of the proximal and distal portions of the expandable body, the sleeve being reversibly expandable with the expandable body from the collapsed state to the expanded state,
wherein the sleeve is adapted to be placed in continuous circumferential contact with a vessel wall adjacent to the proximal portion and the distal portion when the expandable body is in the expanded state, thereby creating an isolated treatment space;
means for deploying the expandable body from the collapsed state to the expanded state; and
at least one catheter tube having proximal and distal ends and access lumen extending therebetween, wherein the catheter tube distal end is coupled to an access port extending through the blood impermeable sleeve such that the access lumen is in fluid communication with the isolated treatment space, the at least one catheter tube extending from the access port into the central lumen and protruding from the proximal portion of the expandable body adjacent the at least one inlet.

16. The vessel isolation system of claim 15, further comprising:
a guidewire coupled to the expandable body.

17. The vessel isolation system of claim 16, wherein the guidewire is slidably coupled to the expandable body at a proximal end of the proximal portion and rotatably coupled to the expandable body at a distal end of the distal portion.

18. The vessel isolation system of claim 16, wherein the guidewire is slidably coupled to the expandable body at a distal end of the distal portion and rotatably coupled to the expandable body at a proximal end of the proximal portion.

19. The vessel isolation system of claim 15, wherein the deploying means is a mechanical linkage that allows the user to mechanically deploy the expandable body.

20. The vessel isolation system of claim 15, wherein the deploying means is a sheath retractable from a position surrounding the expandable body such that when the sheath is retracted, the expandable body is able to expand.

21. The vessel isolation system of claim 15, wherein the expandable body is self-expanding.

* * * * *